(12) United States Patent
Johnson et al.

(10) Patent No.: US 11,868,506 B2
(45) Date of Patent: Jan. 9, 2024

(54) SYSTEMS AND METHODS FOR IMPLEMENTING A SECURE DATABASE FOR STORING A PATIENT OPERATIONAL LONGITUDINAL RECORD

(71) Applicant: TeleTracking Technologies, Inc., Pittsburgh, PA (US)

(72) Inventors: Christopher Johnson, Pittsburgh, PA (US); Michael Coen, Morgantown, WV (US); Jeanne C. Iasella, Pittsburgh, PA (US)

(73) Assignee: TeleTracking Technologies, Inc., Pittsburgh, PA (US)

(*) Notice: Subject to any disclaimer, the term of this patent is extended or adjusted under 35 U.S.C. 154(b) by 848 days.

(21) Appl. No.: 16/721,982

(22) Filed: Dec. 20, 2019

(65) Prior Publication Data

US 2020/0202040 A1    Jun. 25, 2020

Related U.S. Application Data

(60) Provisional application No. 62/784,293, filed on Dec. 21, 2018.

(51) Int. Cl.
*G06F 21/62* (2013.01)
*G16H 10/60* (2018.01)
(Continued)

(52) U.S. Cl.
CPC .......... *G06F 21/6254* (2013.01); *G06F 16/22* (2019.01); *G06F 16/2379* (2019.01); *G06N 20/00* (2019.01); *G16H 10/60* (2018.01)

(58) Field of Classification Search
CPC .. G06F 21/6254; G06F 16/22; G06F 16/2379; G06N 20/00; G16H 10/60; G16H 40/20
See application file for complete search history.

(56) References Cited

U.S. PATENT DOCUMENTS 11,096,577 B2 * 8/2021 Davis, III ............ A61B 5/0002
2013/0124523 A1    5/2013 Rogers et al.
(Continued)

OTHER PUBLICATIONS

Ross et al., ""Big Data" and the Electronic Health Record," Aug. 15, 2014, XP055302245, Retrieved from the Internet: URL:http://www.ncbi.nlm.nih.gov/pmc/articles/PMC4287068/ [retrieved on Sep. 13, 2016].

*Primary Examiner* — Fatoumata Traore
*Assistant Examiner* — Carlton Johnson
(74) *Attorney, Agent, or Firm* — Ference & Associates LLC

(57) ABSTRACT

Systems and methods are disclosed for aggregating and indexing a patient operational longitudinal record and extracting statistics therefrom. In one example, a system for storing and indexing entries in a patient operational longitudinal record may include at least one memory storing instructions and at least one processor configured to execute the instructions to: receive a health update from an authenticated device; map the health update to a health record; apply at least one stored rule to the health update and the health record to determine additional operational data; index and store the health update and the additional operational data in association with the health record; and allow access to the health record based on an associated security protocol.

20 Claims, 7 Drawing Sheets

(51) Int. Cl.
*G06F 16/22* (2019.01)
*G06F 16/23* (2019.01)
*G06N 20/00* (2019.01)

(56) References Cited

U.S. PATENT DOCUMENTS

| | | |
|---|---|---|
| 2013/0291060 A1 | 10/2013 | Moore |
| 2014/0350954 A1 | 11/2014 | Ellis et al. |
| 2017/0147755 A1* | 5/2017 | Lim ........................ G16H 10/60 |
| 2018/0211059 A1* | 7/2018 | Aunger ............... G06F 21/6263 |

* cited by examiner

SYSTEMS AND METHODS FOR IMPLEMENTING A SECURE DATABASE FOR STORING A PATIENT OPERATIONAL LONGITUDINAL RECORD

PRIORITY CLAIM

This application claims priority from U.S. Provisional Application No. 62/784,293, filed Dec. 21, 2018, which is hereby incorporated by reference in its entirety in the present application.

TECHNICAL FIELD

The present disclosure relates generally to the field of aggregation and display of operational patient records. More specifically, and without limitation, this disclosure relates to systems and methods for automatically generating and storing a patient operational longitudinal record from a plurality of networked sources and securely and privately displaying operational records and aggregated statistics therefrom.

BACKGROUND

Traditional mechanisms for maintaining medical records of individuals involve collation of a health record based tests and other patient information gathered during a single point in time, such as a doctor's visit or a hospital stay. Moreover, these health records may be made longitudinal by collating a sufficient number of data points to track visits, prescriptions, and the like over time.

However, an operational flow of a patient through a healthcare system is not accurately captured by such information. Moreover, the operational flow is not fully captured by single data points such as time of admissions, time of bed assignment, and the like.

To extract meaningful operational information with respect to time, manual aggregation and analysis is typically required. However, such manual steps involve privacy concerns regarding whether an analyst may access health information, in addition to incurring inefficiencies and inaccuracies.

SUMMARY

In view of the foregoing, embodiments of the present disclosure describe systems and methods for collating, indexing, and storing a patient operational longitudinal record. The record provided herein uses novel intake systems and stored rules to receive health updates, generate operational data therefrom, and store an operational record including the updates and generated operational data. The operational record may thus comprise logistical information regarding a flow of a patient through a healthcare facility. The logistical information may relate to scheduling and delays of facility events, such as emergency room admission, bed assignment, transport or transfer requests and fulfilment, appointment attendances, and the like. Moreover, the operational record may, similar to a health record, follow a patient from one healthcare facility to another, e.g., by being stored remotely and accessible through a connection to a cloud system storing the record.

In addition, embodiments of the present disclosure provide on-demand access to aggregated statistics from the stored operational record using anonymization and aggregation more efficiently and accurately than extant systems and without violating privacy regulations.

In one embodiment, the present disclosure describes a system for system for storing and indexing entries in a patient operational longitudinal record. The system may comprise at least one memory storing instructions and at least one processor configured to execute the instructions. The at least one processor may execute the instructions to: receive a health update from an authenticated device; map the health update to a health record; apply at least one stored ruled to the health update the health record to determine additional operational data; index and store the health update and the additional operational data in association with the health record; and allow access to the health record based on an associated security protocol.

In another embodiment, the present disclosure describes a system for retrieving aggregated operational statistics from an operational record database. The system may comprise at least one memory storing instructions and at least one processor configured to execute the instructions. The at least one processor may execute the instructions to: receive a request to access one or more aggregated health statistics; authenticate a device sending the request; based on the authentication, select one of a plurality of anonymization rules; retrieve one or more records based on the request and extract information related to the requested one or more statistics from each record; anonymize the extracted information according to the selected anonymization rule; aggregate the anonymized information into the requested one or more statistics; and transmit the one or more statistics to the device.

In some embodiments, the present disclose describes non-transitory, computer-readable media for causing one or more processors to execute methods consistent with the present disclosure.

It is to be understood that the foregoing general description and the following detailed description are example and explanatory only, and are not restrictive of the disclosed embodiments.

BRIEF DESCRIPTION OF THE DRAWINGS

The accompanying drawings, which comprise a part of this specification, illustrate several embodiments and, together with the description, serve to explain the principles disclosed herein. In the drawings.

DETAILED DESCRIPTION

Figure 1A:
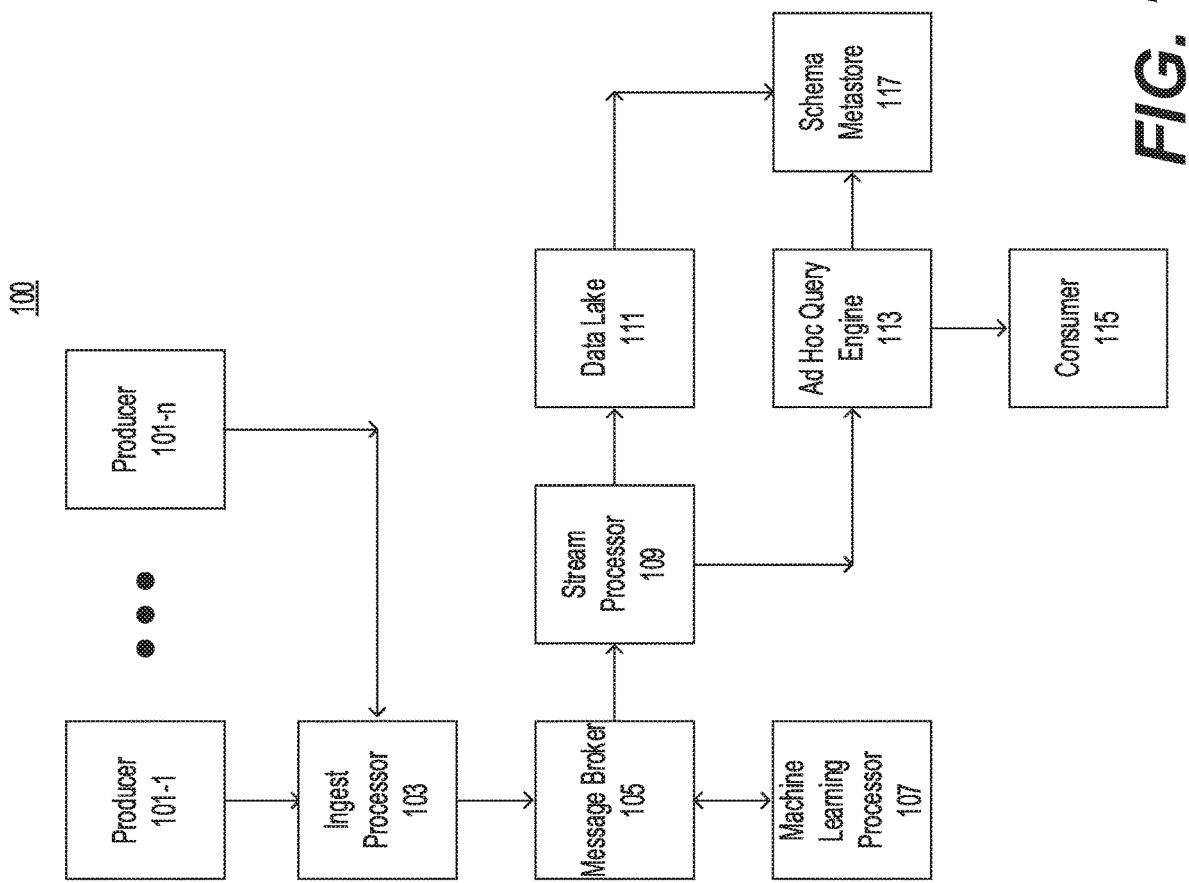
FIG. 1A is a block diagram of a reference architecture for implementing a patient operational longitudinal record, according to an example embodiment of the present disclosure.

The disclosed embodiments relate to systems and methods for collating, indexing, and storing a patient operational longitudinal health record and retrieving and displaying automated and anonymized operational statistics therefrom. Embodiments of the present disclosure may be implemented using a general-purpose computer. Alternatively, a special-purpose computer may be built according to embodiments of the present disclosure using suitable logic elements.

Advantageously, disclosed embodiments may solve the technical problem of using rule-based mechanisms to automate extrapolation of time-dependent information from discrete health updates. This automation allows for generation of an operational longitudinal record, a record that conventional systems do not and cannot generate or use. Moreover, disclosed embodiments may solve the technical problem of providing on-demand and anonymized statistics based on stored records more efficiently and with greater privacy than conventional systems.

According to an aspect of the present disclosure, one or more servers or other computing devices may receive a health update relating to a particular patient. For example, an imaging device (such as an X-ray machine, a computed tomography (CT) scanner, a magnetic resonance imaging (MRI) machine, or the like) may transmit images along with an identifier of a patient (such as a name, a patient ID assigned by a caregiver, a social security number, or the like) to at least one of the servers. Additionally or alternatively, a doctor, surgeon, nurse, or other medical professional may transmit a health update (such as a recordation of an annual physical, a record of a prescription, or the like) to the at least one server.

In another example, a computer associated with a laboratory may transmit test results (e.g., a lipid profile, a creatinine blood test, or the like) to along with an identifier of a patient (such as a name, a patient ID assigned by a caregiver, a social security number, or the like) to at least one of the servers. Additionally or alternatively, a doctor, surgeon, nurse, or other medical professional may transmit a health update (such as notes on lab results, recommended lifestyle changes, or the like) to the at least one server.

In yet another example, a computer associated with an outpatient facility may transmit a health update (such as a record of an appointment, a record of an outpatient surgery, or the like) to at least one of the servers. Additionally or alternatively, a doctor, surgeon, nurse, or other medical professional may transmit a health update (such as a recordation of a checkup, notes based on a surgery, or the like) to the at least one server.

In another example, a computer associated with a pharmacy may transmit a health update (such as a record of a prescription pick-up, a record of a prescription renewal, or the like) to at least one of the servers. Additionally or alternatively, a pharmacist or other medical professional may transmit a health update (such as a notes about a particular prescription, notes about a particular combination of prescriptions, or the like) to the at least one server.

In yet another example, a user device such as a smart phone, a tablet, a wearable device, or the like may transmit a health update (such as a pedometer reading, a heart rate record, a blood pressure record, or the like) to at least one of the servers. Additionally or alternatively, the user may transmit a health update manually to the at least one server.

The updates may be sent over one or more computer networks, such as the Internet, a local area network (LAN), or the like, and may be sent using WiFi, 4G, Ethernet, or the like. In some embodiments, to retain security, the update may be sent over a private network (such as a LAN) and/or may be encrypted (e.g., using an Advanced Encryption Standard (AES)). In embodiments where the update is encrypted, the receiving server may decrypt the request using a private key. In embodiments where the receiving server forwards the update to a different server for storage and indexing, the receiving server may forward the encrypted update without decrypting the update first or may decrypt the update and forward the decrypted update. In embodiments where the receiving server decrypts the update, the decrypted update may be sent along a private channel (such as a private network) to the different server.

When one or more of the servers receives a health update, the server may map the health update to a health record. For example, the server may map the health update based on an identifier included with the health update, such as a name of the user, a social security number of the user, a physical address of the user, or any other information that the server determines is traceable to the user. In another example, the health update may include an anonymized identifier of the user, and the server may use a stored mapping of anonymized identifiers to health records to determine the health record with which the health update is associated. In some embodiments, operations may not be performed on a received health update if the source of the health update cannot be authenticated (e.g., according to the authentication possibilities discussed below with respect to data requests).

Mapping the health update to a health record may occur in a variety of ways. In some embodiments a health update may include data having a key, value and/or key-value pair. This key-value information may be correlated (e.g., by the server) by matching it to key-value information stored on a server receiving the health update or elsewhere in a network to which it is connected (i.e., key-value information for a health record). In some embodiments, if a match between the key-value information in the health update does not match key-value information stored on the server or another device within its network, the health update may not be mapped to a health record, which may cause the server to transmit a warning notification to a source and/or sender of the health update.

Additionally or alternatively, the server may use natural language processing (NLP) to extract an identifier from the health update. For example, the server may extract phrases and snippets of text and other information from the health update and determine that at least one of the phrases or snippets in the health update is an identifier, such as a name of the user, a social security number of the user, a physical address of the user, or any other information that the server determines is traceable to the user.

After mapping the update, the server may apply at least one stored rule to the health update and the health record to determine additional operational data. For example, the server may select from a plurality of stored rules based on contents of the health update. In such an example, the server may use one or more tags included in the health update to select the at least one stored rule, examples of which are shown in Table 1 below.

TABLE 1

| Health Update Tag | Selected Rule |
| --- | --- |
| Time and/or date a patient was seen by a healthcare professional | Subtract time and/or date of scheduling of visit and/or arrival at healthcare professional from time and/or date of being seen |
| Diagnosis and/or admit or transfer request | Subtract time of diagnosis from time of admit or transfer request |
| Name of referring and/or admitting healthcare professional | Add or subtract to declines and acceptances of admitting healthcare professional and/or Subtract time of referral from time of admittance |
| Admission date and/or time | Subtract time of approval from time of bed assignment |
| Therapy administered | Update status of care progression indicator and/or Subtract order time from time of administration |
| Discharge date and/or time | Subtract projected discharge time from actual discharge time and/or Subtract time of discharge from time of availability for next patient |
| Post-acute order | Subtract time of post-acute order from time of bed assignment |
| Ambulatory order | Subtract time of order from time of transport arrival |
| New appointment | Update appointments associated with healthcare professional and/or Update attendance rate associated with patient |

Additionally or alternatively, the server may use natural language processing (NLP) to select the at least one stored rule based on the health update. For example, the server may extract phrases and snippets of text and other information from the health update and determine that at least one of the phrases or snippets in the health update triggers a rule, such as the term "appointment" triggering one or more rules related to appointment, the phase "transfer request" triggering one or more rules related to patient transfers, the name of a healthcare professional triggering a rule to update a record associated with that professional as well as the record associated with the patient, or the like.

The determined operational data output by the at least one stored rule may be related to time rather than comprising a discrete measurement like the health update. For example, the determined operational data may comprise a lag or delay between one even in the health update and another event (either in the same health update or a different health update). In another example, the determined operational data may comprise an aggregate number such as a total number of appointments for a healthcare professional (or a number of appointments per period of time, such as monthly, yearly, or the like), a total number of visits for a patient (or a number of visits per period of time, such as monthly, yearly, or the like), or the like.

After determining the operational data, the server (that received the update or to which the update was forwarded based on the classification) may index and store the health update and the additional operational data in association with the health record. For example, the server may have a plurality of databases with varying security protocols storing the health updates and the operational data. In some embodiments, each database may comprise a relational database storing health updates indexed by an identifier associated with an individual to which the data pertains (medical record identification number, unique patient identifier, unique patient identifier generated from unique patient information, and/or any other data that uniquely identifies pieces of data as pertaining to the same entity) whether anonymized or traceable thereto. Additionally or alternatively, the health updates may be indexed by date and time (of creation and/or of receipt by the server) or any other information included in the updates (such as blood pressure, heart rate, or the like). Accordingly, the databases may be accessed in accordance with a corresponding security protocol and searched by any indices (i.e., identifiers) therein, and such indices may direct a query to multiple databases to find requested information. For example, a query to one database having an indexed record may cause the database to propagate the query to other databases having records with the same index value (i.e. identifier).

In some embodiments, one or more servers may be maintained by a hospital and dedicated to receiving information from devices and computers associated with the hospital and/or otherwise connected to an intranet managed by the hospital. In such embodiments, the different servers may be in communication with each other to store the updates and the operational data in a distributed fashion across the different servers.

The distributed database may be implemented using secure channels between the different servers as well as one or more common indices and/or maps between indices. For example, each server may be dedicated for particular types of data and/or updates from particular devices. Moreover, each server may include a plurality of databases with differing access protocols (e.g., remote database access for SQL, a custom access protocol), and differing security levels. In some embodiments, a server may determine a correct access protocol and/or security level based on an extracted data string. For example, the server may receive a request to access a particular piece of data (e.g., bloodwork testing information for a specific individual) and may extract a database string from the request. The server may then parse the database string to determine identification information (e.g. an encrypted or unencrypted key) for a destination server for the original request, and may use the identification information to determine an access protocol and/or security level for the destination server. This determination may be made by matching the identification information to information stored in a database correlating devices to access protocols and/or security levels.

A query may need to be processed on a plurality of the databases and across a plurality of servers. Accordingly, a server receiving the query may use a map to determine which other servers should be pinged based on the query. Additionally, each server receiving a query or a request from the receiving server may use a map to determine which databases should be searched for health updates responsive to the query.

Accordingly, in some embodiments, another user, such as a medical professional, may request access to an operational record associated with the user. Alternatively, the user may request access to their own operational record. For example, the request may include an identifier of the user for which the operational record is sought, such as a name, a physical address, a social security number, or the like.

In other embodiments, a healthcare executive, or other party authorized to access aggregated information may request metadata or other aggregated operational statistics based on the health updates. Requests may have an associated request type, which may be determined by information input at device initiating the request (e.g., user input to a user interface). Such information may include an individual's name, a patient medical identification number, an insurance number, a type of medical record, a statistic, a timeframe, a care center name, etc. In some embodiments, a request may be tagged as a request for individual patient information or metadata (e.g., to examine a statistical trend). For example, the request may include identifiers of the information requested, such as cholesterol levels, blood pressure, steps walked per day, or the like, and may include limits that comprise sociographic factors (such as age, sex, geography, or the like) or otherwise include indicators of sociographic or other factors related to multiple individuals, by which the results are to be delimited, indexed, and/or sorted. In another example, the request may include a request for one or more specific pieces of operational data across a particular period of time.

A server within the distributed database may receive the request and authenticate the device from which the request was received. Authentication of a requesting device may be determined using single (e.g., a password) or two-factor (e.g., a password and an access code) authentication. In some embodiments, other information, such as an IP address, MAC address, port, etc. may be used to authenticate the requesting device. Authentication information may be contained within the request itself or sent separately from the requesting device. A request (a record pull request, a record update request, etc.) received at the server may not be processed if the requesting device cannot be authenticated, such as due to invalid authentication information. Once authenticated, the server may select one of a plurality of anonymization rules based on an authorization of the device.

Anonymization rules may be implemented using one or more algorithms which, when applied to data, may anonymize it by removing, overwriting, scrambling, etc. identification information from data returned in response to the request. The algorithm may also remove data mappings between pieces of data (e.g., a birthdate is unmapped to an address). Data sent in response to a request may have a degree of anonymization (which may be achieved through a particular anonymization algorithm) selected based on the authorization of the requesting device. For example, a device associated with a medical professional may be authorized to receive non-anonymized records, operational statistics, or metadata while a device associated with a research institution or a healthcare executive may be authorized only to receive anonymized metadata or operational statistics. In other embodiments, data may be partially de-anonymized; for example, identifying pieces of data may be sent only on a need-to-know basis, and other data may be anonymized. In some embodiments, after authenticating the requesting device, the device receiving the request (e.g., server) may query a directory to determine the access rights corresponding to the requesting device. The directory may link different access rights to different devices, organizations, etc. based on a policy implemented by, for example, a health system associated with the device receiving the request.

The receiving server may then ping other servers in the distributed database to return health updates responsive to the request. For example, as explained above, the receiving server may determine which other servers to ping based on a mapping of the request to a map associated with the distributed database. The receiving server may also anonymize extracted information according to the selected anonymization rule in addition to aggregating the extracted information into the requested metadata.

The receiving server may include an indication of the requestor's authorization or may forward the request in full for independent authorization by the different servers. In the latter embodiments, the distributed database may be protected against a single rogue server and/or an attack on a single server.

The receiving server and any other server pinged by the receiving server may generate a database query corresponding to the request, based on any of the information contained in the request. For example, a request for an operational record associated with a particular user may result in a query to pull all updates indexed to an identifier of the particular user. The server may adjust the identifier to match the identifier(s) by which the database on which the query will be run is indexed. For example, the request may include a social security number, and the server may generate a query with a name or date of birth if one or more databases on the server storing health updates is indexed by name or date of birth and not by social security number. To perform such an adjustment, the server may use a map that relates some identifiers of a user to other identifiers of a user. In some embodiments, the server may ping one or more other servers to perform the transformation. For example, the server may determine that another server has a database with social security numbers and names both indexed and may send a request to the other server to transform the social security number of the request to a corresponding name for use in the server's databases.

The server may execute generated queries on appropriate databases. For example, the server may determine that the request is for a full operational record and may execute appropriate queries. In another example, the server may determine that the request is for metadata or operational statistics and may execute appropriate queries as well as any aggregation required to transform the operational data into aggregated metadata or statistics. In addition to executing the queries, as explained above, the server may perform the appropriate anonymization (which may be an anonymization process selected based on a policy implemented by the server, the server's network, an organization of the server, the requestor, etc.). For example, if the request is for metadata, the server may execute appropriate queries and then scrub (remove) all traceable identifiers from the results and instead assign a randomized identifier to the scrubbed results (or remove identifiers altogether, if the metadata requested is only operational). A user may use this randomized identifier to track information associated with an individual or save information for later analysis, while being prevented from using original identifiers to find identifying information of the individual. Alternatively, the server may execute appropriate queries such that only certain portions of updates are pulled from the databases, such as blood pressure, cholesterol levels, or the like, and that any traceable identifiers are not pulled for the results. The server may then assign a randomized identifier to the results, e.g., if the metadata requested is for research purposes.

In some embodiments, anonymized and identifying (i.e., un-anonymized) data corresponding to the same underlying information may be stored in separate storage devices or separate partitions of the same storage device. For example, a first database may hold identifying information for patients (e.g., medical records containing Social Security numbers), and a second database may hold the same information in anonymized form. The first database may be subject to heightened security (encryption techniques, access restrictions, etc.), relative to the second database. By anonymizing and storing anonymous data separately, prior to receiving a request, requests for anonymous data may be fulfilled with faster speed, as the information is readily available. Such anonymization and storage much occur when new (i.e., identifying) data is created (such as when a patient undergoes a medical test), may be done periodically (e.g., every night), or may be done in any other way to create and store anonymized data when computing resource usage is low. Generating operational data may be done in the same manner.

The sever may then collate its own results and results received from other servers based on their queries to their databases. The user may therefore receive, in response to the request, a data serialized format including the operational record(s), statistics, and/or metadata. For example, the data serialized format may comprise a JavaScript Object Notation (JSON) file, an Extensible Markup Language (XML) file, or the like.

Additionally or alternatively, one or more of the servers may generate a graphical user interface including visual representations of the operational record, statistics, and/or metadata. Graphical representations may include pie charts, bar graphs, and other visual representations of the received data. The graphical interfaces may also include text and numbers displaying the received data. In some embodiments, displayed information may be altered based on a filter selected at the graphical user interface (e.g., filter received data to only data: of actions within the past week, associated with female individuals, within a certain geography, etc.).

In FIG. 1A, there is shown a block diagram of a system 100 for implementing a patient operational longitudinal record. As depicted in FIG. 1A, system 100 may comprise a plurality of producers 101-1, . . . , 101-n producing health updates for a patient operational longitudinal record. For example, ingest processor 103 (which may comprise a portion of one or more servers, e.g., server 500 of FIG. 5), may include one or more APIs, such as a mobile API communicating with mobile devices (e.g., device 600 of FIG. 6) and/or wearable devices, a medical provider API communicating with devices used by healthcare professionals and/or medical imaging or testing devices, or the like. As depicted in FIG. 1A, ingest processor 103 receives health updates from the plurality of produces, which may comprise a user device, such as a mobile device 600 of FIG. 6 or a wearable device, one or more medical devices, computers associated with hospitals and outpatient offices computers associated with an insurance company, or the like. In some embodiments, ingest processor 103 may comprise an Apache Ambari system, an Apache NiFi system, an Apache Zookeeper system, or the like. In such an example, producers may use an Apache MiNiFi protocol to send health updates to ingest processor 103.

In some embodiments, one or more of the APIs of ingest processor 103 may require connection to a private network (and/or to a virtual private network (VPN)) for requests to be received. This may, for example, allow for health updates to remain unencrypted without significant risk of interception.

As further depicted in FIG. 1A, message broker 105 may queue health updates from ingest processor 103 for additional processing (e.g., by machine learning processor 107, by one or more stored rules to determine additional operational data, as explained below, or the like). For example, message broker 105 may queue health updates based on which stored rules will be applied, which may be selected as explained above. In one example, message broker 105 may comprise an Apache Kafka system, an Apache Ambari system, an Apache Zookeeper system, or the like.

As further depicted in FIG. 1A, message broker 105 may channel the health updates and any additional data generated therefrom (e.g., from stored rules generating additional operational data, from machine learning processor 107, or the like) to a stream processor 109. Stream processor 109 may prepare the health updates and additional data for storage, e.g., via extract, transform, load (ETL) procedures, applying one or more cleansing and/or standardization techniques, indexing the health updates and additional information by one or more identifiers of existing operational records, or the like. In some embodiments, in addition to or in lieu of message broker 105, stream processor 109 may select and apply one or more rules for generation of additional operational data from the health updates channeled by message broker 105. In one example, stream processor 109 may comprise an Apache Spark system, an Apache Airflow system, or the like.

In addition to storing processed health updates and additional data in data lake 111 (which may comprise an Amazon S3 storage or the like), stream processor 109 may direct queries from users (e.g., consumer 115) to ad-hoc query engine 113. Ad-hoc query engine 113 may comprise a copy of data lake 111 in a relational database format (e.g., structure query language (SQL) format or the like) upon which user queries may be executed. Alternatively, although not depicted in FIG. 1A, ad-hoc query engine 113 may retrieve data from data lake 111 and parse the retrieved data into a query response in response to queries as they are received. For example, schema metadata 117 may define a relational structure of health updates and additional data stored in data lake 111 to allow ad-hoc query engine 113 to perform the retrieval and parsing. In one example, schema metadata 117 may comprise an Apache Hive Metastore.

In some embodiments, any authorized query received by stream processor 109 may be allowed to access all information within data lake 111 (or the copy of data lake 111 comprising ad-hoc query engine 113). In other embodiments, one or more consumers may be restricted. For example, consumer 115 may lack read privileges for non-anonymized information from data lake 111. In such embodiments, ad-hoc query engine 113 may anonymize results before returning them to consumer 115. In another example, consumer 115 may lack read privileges for certain types of information from data lake 111. In such embodiments, ad-hoc query engine 113 may strip any non-authorized information from results before returning them to consumer 115. In one example, ad-hoc query engine may comprise an Amazon Redshift system or the like.

Figure 1B:
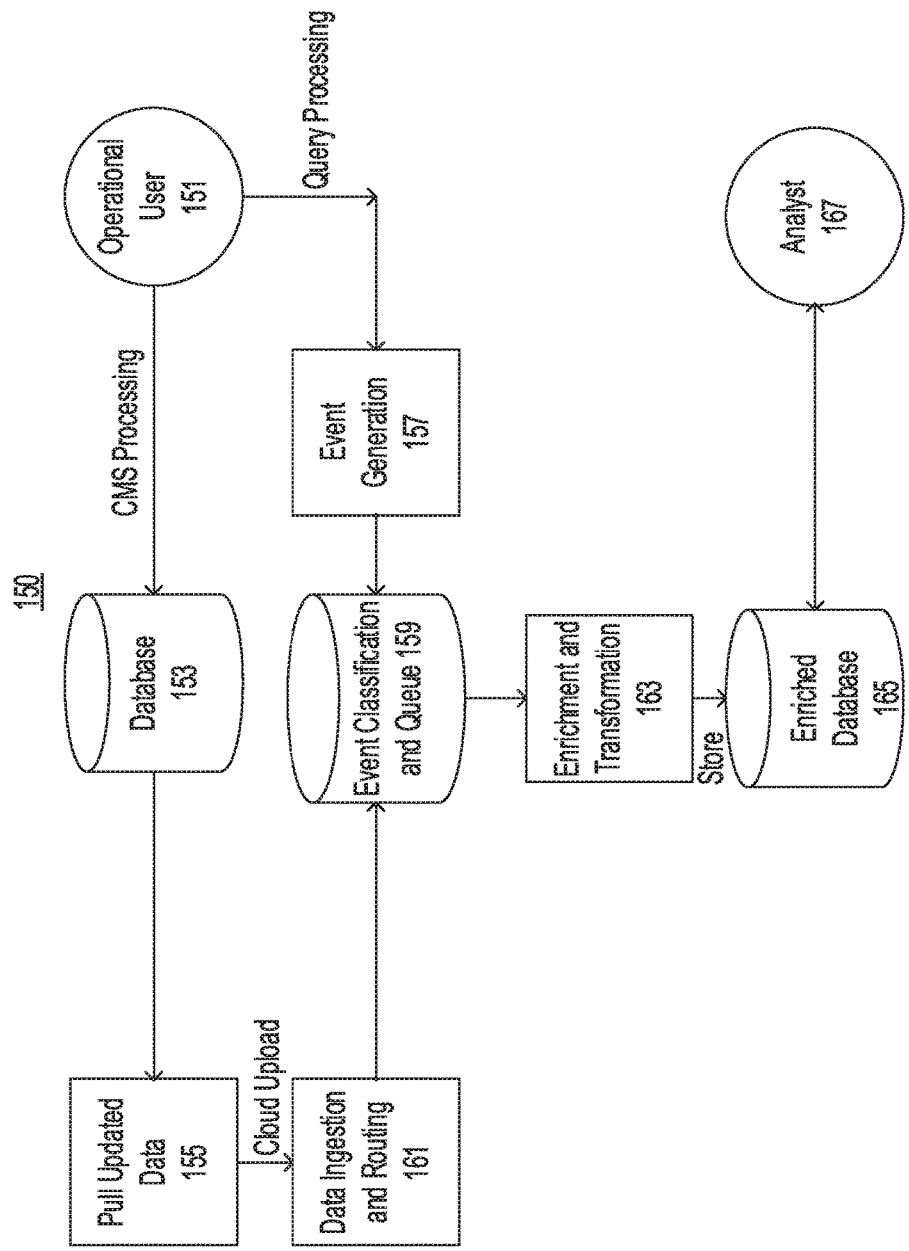
FIG. 1B is a block diagram of data flows within the reference architecture of FIG. 1A, according to an example embodiment of the present disclosure.

FIG. 1B is a block diagram of data flows 150 within the reference architecture 100 of FIG. 1A. For example, operational user 151 may comprise a producer providing a health update to the system. The health update may undergo CMS processing for local storage in database 153, e.g., within an extant system used by a healthcare system to track patient records and billing. Concurrently, the health update may undergo query processing in order to generate an event at step 157. For example, the event may comprise additional operational data, as explained above, and/or one or more updates to additional records (e.g., associated with a healthcare professional) based on the health update. Accordingly, generation of the event may comprise application of at least one stored rule to the health update to generate additional information.

As further depicted in FIG. 1B, the cloud system that generated additional information 159 based on a health update may also pull any related updates (e.g., based on a common unique identifier, such as a medical record number)

from local database 153 (step 155) and perform data ingestion and routing (step 161, e.g., using ingest processor 103 and/or message broker 105 of FIG. 1A) to associate any relevant health updates with the additional information 159. For example, a person may move from a hospital bed to a surgery unit in real time, which may be reflected by input at a device (e.g., user input at caretaker computer) and/or sensor information (e.g., infrared sensors, RFID tags, etc. sensing movement of the person to the surgery unit) and a message is sent to prompt a server or server to update data. Further enrichment (e.g., using machine learning processor 107) and transformation (e.g., using stream processor 109) at step 163 may prepare the health update(s) and additional information for storage 165 (e.g., date lake 111 of FIG. 1A). An analyst 167 or any other person authorized to access at least some information from the patient operational longitudinal records may execute a query on storage 165, e.g., via ad-hoc query engine 113 of FIG. 1A.

Figure 2:
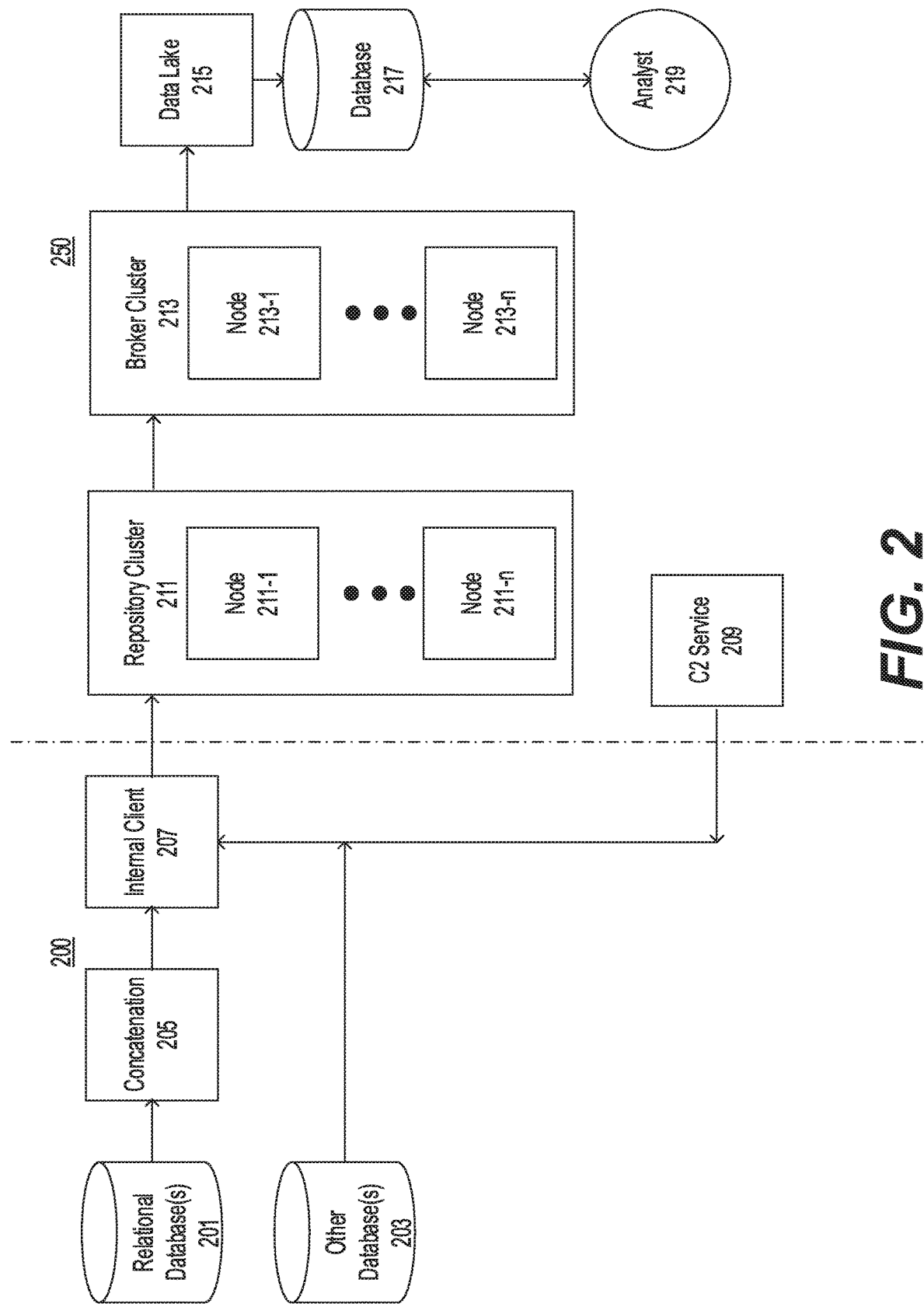
FIG. 2 is a block diagram of a reference architecture for asynchronous data ingestion for a longitudinal operational record, according to an example embodiment of the present disclosure.

FIG. 2 depicts a block diagram of an on-site system 200 and a cloud system 250 cooperating for implementing a patient operational longitudinal record database. Although depicted as divided in FIG. 2, any of the components of on-site system 200 may additionally or alternatively be implemented in a cloud environment. Similarly, any of the components of cloud system 250 may additionally or alternatively be implemented on-premise. For example, on-site system 200 may comprise database 152 of FIG. 1B while cloud system 250 comprises the other components of system 150 of FIG. 1B. As depicted in FIG. 2, on-site system 200 may comprise one or more relational databases, such as database(s) 201, as well as one or more additional databases (e.g., unstructured data lakes, graphical databases, or the like), such as database(s) 203. Both database(s) 201 and database(s) 203 may provide updates to an internal client 207 (and/or to a C2 client of cloud system 250 via internal client 207). In some embodiments, one or more structured query operations (such as a SQL VIEW operation) may be used to perform concatenation 205 data from relational database(s) 201 before providing data to internal client 207. In some embodiments, a device may pull information stored in a database (e.g., in another table) and may present it as an aggregated representation, such as within a database table. A user may then manipulate the database table to achieve a different view, subset of information, etc., without changing the underlying data stored in the database. For example, a model may exist as an intermediary between a user device and a database, such as according to Command Query Responsibility Segregation (CQRS). This arrangement may be used for data aggregation that has been frequently requested of a database in the past, and may speed data transfer to a user. In some embodiments, if a user's manipulation of the database table or model, such changes can be propagated to the underlying database after the user finishes operations.

As further depicted in FIG. 2, cloud system 250 may comprise a repository cluster 211 and broker cluster 213. Each cluster may include one or more nodes, e.g., repository cluster 211 includes nodes 211-1, . . . 211-*n*, and broker cluster 213 includes nodes 213-1, . . . 213-*n*. Although depicted with the same number of nodes, repository cluster 211 and broker cluster 213 may comprise different numbers of nodes depending on the needs and configuration of the facility implementing the disclosed systems. Repository cluster 211 may process updates from on-site system 200 (e.g., similar to ingest processor 103 of FIG. 1A), and broker cluster 213 (e.g., similar to message broker 105 of FIG. 1A) may channel updates from repository clusters 211, along with any additional information generated therefrom, to data lake 215.

In addition, data lake 215 may be copied into a relational structure such as database 217 (e.g., provided by ad-hoc query engine 113 of FIG. 1A). As depicted in FIG. 2, an analyst 219 or any other person authorized to access at least some information from the operational longitudinal records may execute a query on database 217, e.g., via ad-hoc query engine 113 of FIG. 1A.

Figure 3:
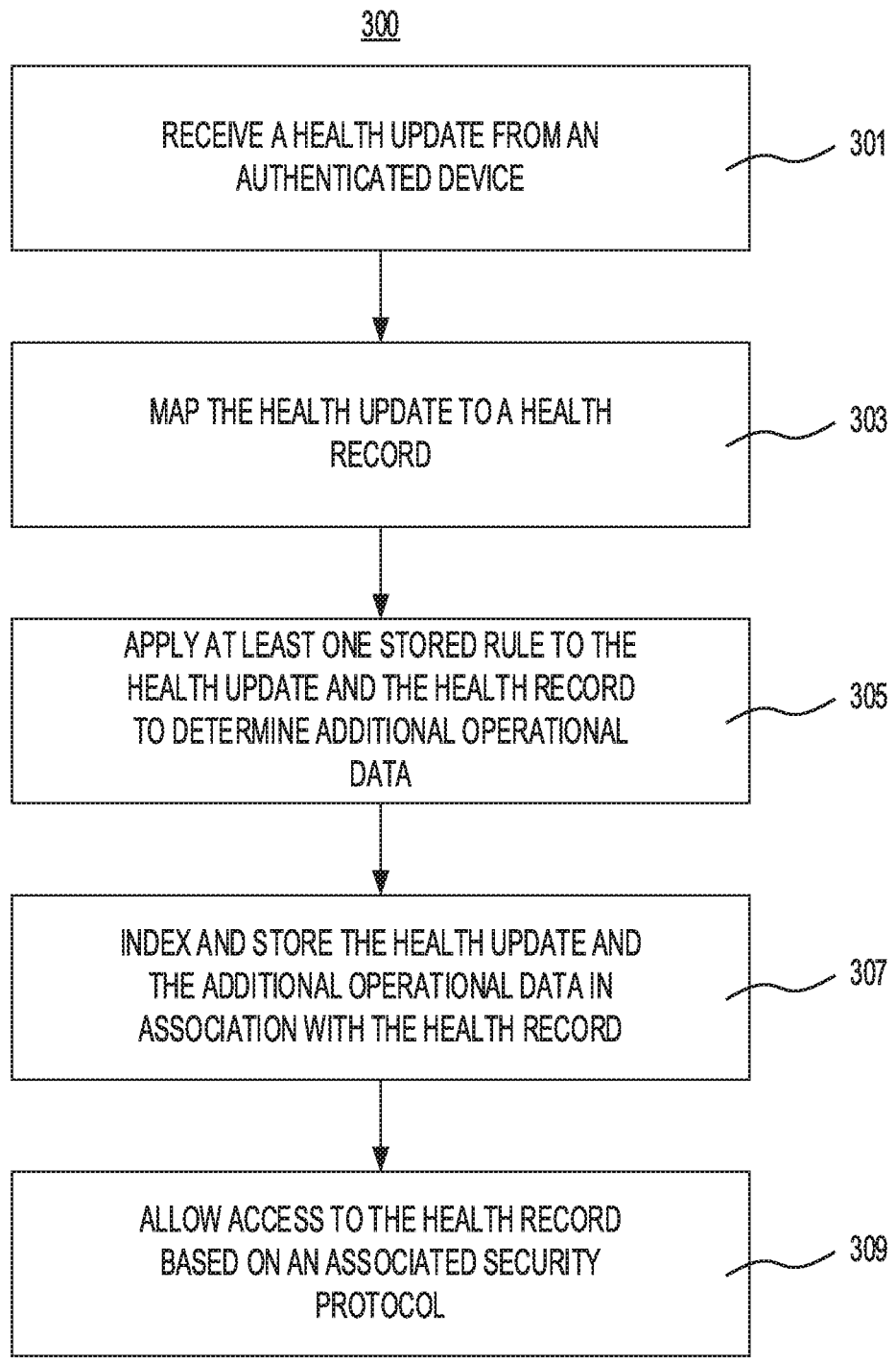
FIG. 3 is a flowchart of an example method for storing and indexing entries in a patient operational longitudinal record, according to an example embodiment of the present disclosure.

FIG. 3 depicts an example method 300 for storing and indexing health entries in an operational longitudinal record. Method 300 may be implemented using one or more processors (e.g., processor 503 of FIG. 5).

At step 301, the processor may receive a health update from an authenticated device. For example, the device may comprise a device (such as an X-ray machine, a computed tomography (CT) scanner, a magnetic resonance imaging (MRI) machine, or the like); a computer associated with a hospital, an outpatient facility, a gym, or the like; a wearable device such as a Fitbit®, a smart phone, or other user device; or the like. The health update may be sent over one or more computer networks, such as the Internet, a local area network (LAN), or the like, and may be sent using WiFi, 4G, Ethernet, or the like. In some embodiments, to retain security, the health update may be sent over a private network (such as a LAN) and/or may be encrypted (e.g., using an Advanced Encryption Standard (AES)). In embodiments where the health update is encrypted, the processor may decrypt the health update using a private key.

The device may be authenticated by the processor. For example, the health update may include a key or other private identifier of the device that the processor may use to verify that the health update is coming from a device authorized to write health updates to the distributed database.

At step 303, the processor may map the health update to a health record. For example, as explained above, the processor may map the health update using one or more identifiers included in or extracted from the health update.

At step 305, the processor may apply at least one stored rule to the health update and the health record to determine additional operational data. For example, the processor may select at least one rule based on contents of the health update, as explained above with reference to the examples of Table 1. In some embodiments, the additional operational data may comprise an extraction that is, at least partially, temporal in nature based on the health update and the health record. Additionally or alternatively, the additional operational data may comprise an update to a different record, e.g., that associated with a healthcare professional, that is, at least partially, temporal in nature. In some embodiments, a device may use a machine learning algorithm to derive data and make suggestions to a user. For example, a device may detect a past correlation between a health update and changes to other data (either manually or automatically), and suggest creating, modifying, or deleting operational data or underlying data of a user. Based on operational data created over time, the system may learn which operational data to create and when to create it (i.e., correct triggering actions). This machine learning process may alter stored rules for operational data and/or derived data.

At step 307, the processor may index and store the health update and the additional operational data in association with the health record. For example, as explained above with respect to FIG. 1A, the health update and the additional operational data may be stored in a data lake and indexed to an identifier of the health record and/or stored in a relational database maintained by an ad-hoc query engine.

At step 309, the processor may allow access to the health record based on an associated security protocol. For example, some consumers may have access to only portions of health updates, operational statistics, or metadata stored and indexed therein (or to anonymized health updates and/or metadata). On the other hand, other consumers may have access to detailed records, statistics, and metadata without restriction. Such access may be achieved through an encrypted stream between a requesting device (e.g., user device) and a data-hosting device (e.g., server, database, data lake, etc.).

Method 300 may include additional steps. For example, method 300 may further include forwarding the health update to one or more other servers for additional or alternative storage thereon (e.g., to database 217 in addition to data lake 215).

Additionally or alternatively, method 300 may include applying one or more thresholds or other rules to the additional operational data and, if the thresholds or other rules are satisfied, generating and transmitting an alert. For example, if a delay between admission and bed assignment exceeds a threshold, a nurse or other healthcare professional may receive an alert such that the professional may take action to reduce the current and/or future delays for the same patient. In another example, if a delay between discharge and bed cleaning exceeds a threshold, an executive or other manager may receive an alert such that the manager may take action to ensure the bed is turned around without further delay.

Figure 4:
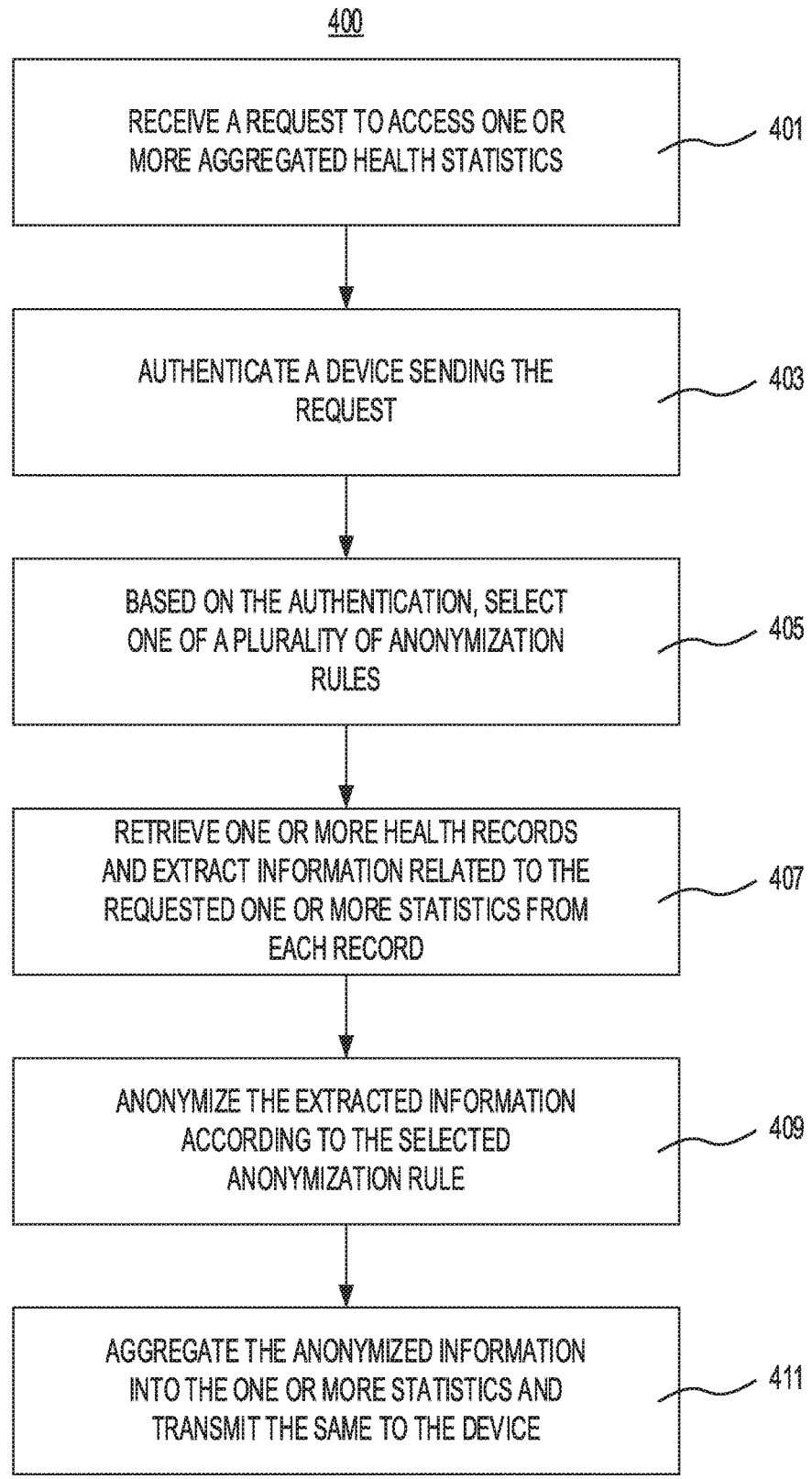
FIG. 4 is a flowchart of an example method for retrieving aggregated operational statistics from an operational record database, according to an example embodiment of the present disclosure.

FIG. 4 depicts an example method 400 for retrieving aggregated operational statistics from an operational record database. Method 400 may be implemented using one or more processors (e.g., processor 503 of FIG. 5).

At step 401, the processor may receive a request to access one or more aggregated health statistics. The request may be sent over one or more computer networks, such as the Internet, a local area network (LAN), or the like, and may be sent using WiFi, 4G, Ethernet, or the like. In some embodiments, to retain security, the request may be sent over a private network (such as a LAN) and/or may be encrypted (e.g., using an Advanced Encryption Standard (AES)). In embodiments where the request is encrypted, the processor may decrypt the request using a private key.

At step 403, the processor may authenticate a device sending the request. For example, the processor may verify a key or other private identifier of the device included in the request to verify that the request is coming from a device authorized to read health updates from the distributed database.

At step 405, based on the authentication, the processor may select one of a plurality of anonymization rules. For example, the processor may determine that a request is authorized only for anonymized metadata, such as cholesterol levels, steps walked, or the like. Additionally or alternatively, the processor may determine that a request is authorized only for aggregated operational statistics, such as average wait times, average admission times, average bed turnaround times, or the like. Additionally or alternatively, the processor may determine that a request is authorized for one or more full records and associated operational statistics related to the record(s).

At step 407, the processor may retrieve one or more records based on the request and extract information related to the requested one or more statistics from each record. For example, as explained above, the processor may retrieve the records from a relational database or from a data lake using associated schema definitions. In some embodiments, different queries may be generated and executed to retrieve anonymized data as compared to full records.

At step 409, the processor may anonymize the extracted information according to the selected anonymization rule. For example, the processor may replace any identifiers traceable to one or more patients with anonymized identifiers. In embodiments where only aggregated statistics are requested, the processor may remove identifiers altogether.

At step 411, the processor may aggregate the anonymized information into the requested one or more statistics and transmit the one or more statistics to the device. For example, the processor may generate a data serialized format including the one or more statistics that combines the data received from the one or more servers (as well as any data retrieved locally). For example, the data serialized format may comprise a JavaScript Object Notation (JSON) file, an Extensible Markup Language (XML) file, or the like.

The one or more statistics may be sent over one or more computer networks, such as the Internet, a local area network (LAN), or the like, and may be sent using WiFi, 4G, Ethernet, or the like. In some embodiments, to retain security, the record may be sent over a private network (such as a LAN) and/or may be encrypted (e.g., using an Advanced Encryption Standard (AES)). In embodiments where the record is encrypted, the device may decrypt the request using a private key.

Method 400 may include additional steps. For example, as explained above, method 400 may further include generating one or more interfaces for visualizing the requested statistics. In such an example, the processor may transmit the one or more interfaces to the device in addition to or in lieu of a data serialized format comprising the statistics.

Additionally or alternatively, method 400 may include applying one or more thresholds or other rules to the requested statistics and, if the thresholds or other rules are satisfied, generating an alert for inclusion in a report with the statistics and/or concurrent transmission with the statistics. For example, if aggregate delays between admission and bed assignment exceed a threshold, an alert may draw attention to the delays such that a viewer of the statistics may take action to reduce such delays within an associated healthcare system. In another example, if aggregate delays between discharge and bed cleaning exceed a threshold, an alert may draw attention to the delays such that a viewer of the statistics may take action to reduce such delays within an associated healthcare system.

Figure 5:
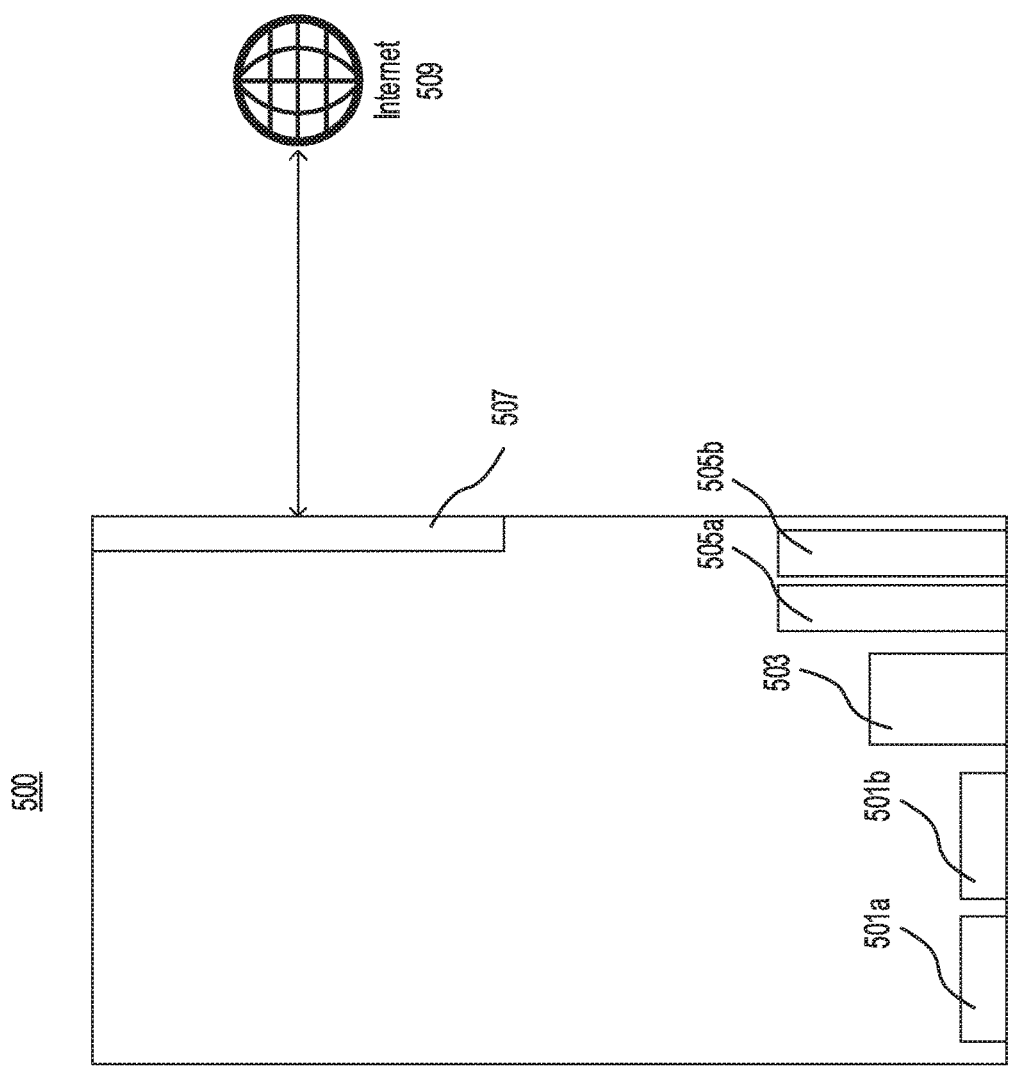
FIG. 5 is a block diagram of an example server with which the systems, methods, and apparatuses of the present disclosure may be implemented.

FIG. 5 is block diagram of an example device 500 suitable for implementing the disclosed systems and methods. For example, device 500 may execute method 300 of FIG. 3 and/or method 400 of FIG. 4. Device 500 may comprise a server, desktop computer, or the like. For example, device 500 may implement the functions depicted in the architectures of FIGS. 1A, 1B, and 2.

As depicted in FIG. 5, example server 500 may include at least one processor (e.g., processor 503) and at least one memory (e.g., memories 505a and 505b).

Processor 503 may comprise a central processing unit (CPU), a graphics processing unit (GPU), or other similar circuitry capable of performing one or more operations on a data stream. Processor 503 may be configured to execute instructions that may, for example, be stored on one or more of memories 505a and 505b.

Memories 505a and 505b may be volatile memory (such as RAM or the like) and/or non-volatile memory (such as flash memory, a hard disk drive, or the like). As explained above, memories 505a and 505b may store instructions for execution by processor 503.

As further depicted in FIG. 5, server 500 may include at least one network interface controller (NIC) (e.g., NIC 507). NIC 507 may be configured to facilitate communication over at least one computing network (e.g., network 509, which is depicted in the example of FIG. 5 as the Internet). Communication functions may thus be facilitated through one or more NICs, which may be wireless and/or wired and may include an Ethernet port, radio frequency receivers and transmitters, and/or optical (e.g., infrared) receivers and transmitters. The specific design and implementation of the one or more NICs depend on the computing network 509 over which server 500 is intended to operate. For example, in some embodiments, server 500 may include one or more wireless and/or wired NICs designed to operate over a GSM network, a GPRS network, an EDGE network, a Wi-Fi or WiMax network, and a Bluetooth® network. Alternatively or concurrently, server 500 may include one or more wireless and/or wired NICs designed to operate over a TCP/IP network.

As depicted in FIG. 5, server 500 may include and/or be operably connected to one or more storage devices, e.g., storages 501a and 501b. Storage devices 501a and 501b may be volatile (such as RAM or the like) or non-volatile (such as flash memory, a hard disk drive, or the like).

Processor 503, memories 505a and 505b, NIC 507, and/or storage devices 501a and 501b may comprise separate components or may be integrated in one or more integrated circuits. The various components in server 500 may be coupled by one or more communication buses or signal lines (not shown).

Figure 6:
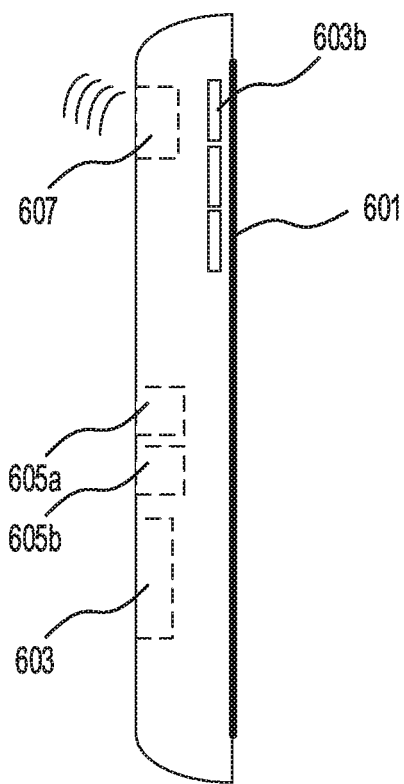
FIG. 6 is a block diagram of an example user device for collecting and generate data for inclusion in a patient operational longitudinal record and/or retrieving statistics from the same, according to embodiments of the present disclosure.

FIG. 6 is block diagram of an example user device for providing health updates to an operational record database and/or requesting aggregated statistics from the same. Device 600 may comprise a smartphone, a tablet, a wearable like a Fitbit®, or the like.

Device 600 may have a screen 601. For example, screen 601 may display one or more graphical user interfaces (GUIs). In certain aspects, screen 601 may comprise a touchscreen to facilitate use of the one or more GUIs.

As further depicted in FIG. 6, device 600 may have at least one processor 603. For example, at least one processor 603 may comprise a system-on-a-chip (SOC) adapted for use in a portable device, such as device 600. Alternatively or concurrently, at least one processor 603 may comprise any other type(s) of processor.

As further depicted in FIG. 6, device 600 may have one or more memories, e.g., memories 605a and 605b. In certain aspects, some of the one or more memories, e.g., memory 605a, may comprise a volatile memory. In such aspects, memory 605a, for example, may store one or more applications (or "apps") for execution on at least one processor 603. For example, an app may include an operating system for device 600 and/or an app for providing health updates to and/or requesting aggregated statistics from a patient operational longitudinal record database. In addition, memory 605a may store data generated by, associated with, or otherwise unrelated to an app in memory 605a.

Alternatively or concurrently, some of the one or more memories, e.g., memory 605b, may comprise a non-volatile memory. In such aspects, memory 605b, for example, may store one or more applications (or "apps") for execution on at least one processor 603. For example, as discussed above, an app may include an operating system for device 600 and/or an app for providing health updates to and/or requesting aggregated statistics from a patient operational longitudinal record database. In addition, memory 605b may store data generated by, associated with, or otherwise unrelated to an app in memory 605b. Furthermore, memory 605b may include a pagefile, swap partition, or other allocation of storage to allow for the use of memory 605b as a substitute for a volatile memory if, for example, memory 605a is full or nearing capacity.

As depicted in FIG. 6, device 600 may include at least one network interface controller (NIC) (e.g., NIC 607). NIC 607 may be configured to facilitate communication over at least one computing network. Communication functions may thus be facilitated through one or more NICs. Although depicted in wireless in FIG. 6 and including radio frequency receivers and transmitters and/or optical (e.g., infrared) receivers and transmitters, NIC 607 may alternatively be wired and include an Ethernet port or the like. The specific design and implementation of the one or more NICs depend on the computing network over which user interface device 600 is intended to operate. For example, in some embodiments, user interface device 600 may include one or more wireless and/or wired NICs designed to operate over a GSM network, a GPRS network, an EDGE network, a Wi-Fi or WiMax network, and a Bluetooth® network. Alternatively or concurrently, user interface device 600 may include one or more wireless and/or wired NICs designed to operate over a TCP/IP network.

Each of the above identified instructions and applications may correspond to a set of instructions for performing one or more functions described above. These instructions need not be implemented as separate software programs, procedures, or modules. Disclosed memories may include additional instructions or fewer instructions. Furthermore, user device 600 may securely deliver health updates to server 500. For example, user device 600 may send a health update to server 500, and server 500 may execute method 300 of FIG. 3. Additionally or alternatively, user device 500 may request health statistics from server 500, and server 500 may execute method 400 of FIG. 4. These functions of user device 600 may be implemented in hardware and/or in software, including in one or more signal processing and/or application specific integrated circuits.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented with hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive.

Instructions or operational steps stored by a computer-readable medium may be in the form of computer programs, program modules, or codes. As described herein, computer programs, program modules, and code based on the written description of this specification, such as those used by the processor, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A system for storing and indexing entries in a patient operational longitudinal record, the system comprising:
    at least one memory storing instructions; and
    at least one processor configured to execute the instructions to perform operations comprising:
        receiving, at a server of a healthcare system, a health update relating to a particular patient from a device corresponding to the healthcare system;
        mapping, at the server, the health update to a health record of the particular patient by correlating information traceable to the particular patient contained within the health update to identifying information of the health record;
        applying, by the server, at least one stored rule to the health update and the health record to determine operational data comprising information related to a flow of a patient through a healthcare system, wherein the applying comprises selecting the at least one stored rule from a plurality of stored rules based upon at least one tag included within the health update and based upon additional information, identified using natural language processing, included within the health update;
        indexing and storing, by the server and within a data store of the healthcare system, the health update and the operational data in association with the health record; and
        allowing access to the health record, within the data store and in response to receiving a query to access the health record, based on an associated security protocol of the data store and an access authorization of a user providing the query.

2. The system of claim 1, wherein the at least one stored rule is generated from a machine learning algorithm.

3. The system of claim 1, wherein the security protocol prescribes a degree of access based on an authorization of a requesting device.

4. The system of claim 3, wherein the authorization of the requesting device is determined based on a data string extracted from a request of the requesting device.

5. The system of claim 1, wherein the health update and health record are associated with a single individual.

6. The system of claim 5, the operations further comprising mapping the health update based on a unique identifier included in the request, the unique identifier identifying the single individual.

7. The system of claim 5, wherein the operational data is associated with the single patient.

8. The system of claim 1, the operations further comprising authenticating the device, wherein mapping the health update to the health record is based on the authentication.

9. The system of claim 1, wherein the storing comprises:
    storing the health record in a first database; and
    storing the operational data in a second database.

10. The system of claim 9, wherein the indexing comprises:
    indexing the health record and the operational data with the same identifier.

11. A system for retrieving aggregated operational statistics from an operational record database, the system comprising:
    at least one memory storing instructions; and
    at least one processor configured to execute the instructions to perform operations comprising:
        receiving, at a receiving server of a healthcare system, a request comprising at least one search criteria to access one or more aggregated operational statistics, wherein the aggregated operational statistics are stored within at least one data store of the healthcare system, wherein each of the at least one data stores have an associated security protocol identifying access authorization restrictions for information contained within each of the at least one data stores, wherein the one or more aggregated operational statistics are generated from health records and corresponding health updates of patients within the healthcare system, wherein the one or more aggregated operational statistics are generated from the health records and corresponding health updates by the receiving server applying at least one stored rule to the health updates and the health records of the patients, wherein the at least one stored rule is identified based upon at least one tag included within the health update and based upon additional information, identified using natural language processing, included within the health update;
        authenticating a device sending the request;
        selecting one of a plurality of anonymization rules based upon access rights of the device, wherein the plurality of anonymization rules identify information within the one or more aggregated operational statistics that need to be anonymized in a response to the request based upon the access rights;
        retrieving one or more records based on the request and extract information related to the requested one or more statistics from each record, wherein the retrieving comprises the receiving server querying other servers to return health updates responsive to the request, wherein the querying comprises the receiving server adjusting at least a portion of the at least one search criteria to match an indexing of search criteria of a given of the other servers;

anonymizing the extracted information according to the selected anonymization rule, wherein the anonymizing comprises modifying at least a portion of the extracted information based upon the access rights of the device;

aggregating the anonymized information into the requested one or more statistics; and transmitting the one or more statistics to the device.

12. The system of claim 11, the operations further comprising determining authorization of the device, wherein the selected anonymization rule is selected based on the determined authorization.

13. The system of claim 11, wherein the one or more records are stored in one or more databases.

14. The system of claim 11, the operations further comprising extracting a data string from the request.

15. The system of claim 14, the operations further comprising identifying the one or more records based on the extracted data string.

16. The system of claim 11, wherein the request contains an identifier of information requested.

17. The system of claim 16, wherein the one or more records are selected from among a dataset based on the identifier.

18. The system of claim 16, wherein a first portion of the one or more records are retrieved from a first database and the first database propagates the request to a second database.

19. The system of claim 18, wherein a second portion of the one or more records are retrieved from the second database on the identifier.

20. The system of claim 11, wherein the statistics are transmitted to a database table viewable by the device.

* * * * *